United States Patent [19]

Farooq et al.

[11] 4,175,137
[45] Nov. 20, 1979

[54] ETHERIFIED CYCLOALKANOLS

[75] Inventors: Saleem Farooq, Ettingen; Friedrich Karrer, Zofingen; Georges Haas, Binningen, all of Switzerland

[73] Assignee: Ciba-Geigy Corporation, Ardsley, N.Y.

[21] Appl. No.: 924,315

[22] Filed: Jul. 13, 1978

[30] Foreign Application Priority Data

Jul. 20, 1977 [CH] Switzerland .......................... 9002/77

[51] Int. Cl.² .............................................. A01N 9/12
[52] U.S. Cl. .................................. 424/337; 260/609 F; 424/341; 568/637; 568/638; 568/640; 568/641
[58] Field of Search .................... 260/613 R, 609 F; 568/638, 640, 637, 641; 424/337, 341

[56] References Cited

U.S. PATENT DOCUMENTS

| | | | |
|---|---|---|---|
| 3,098,105 | 7/1963 | Reifschneider | 260/609 F |
| 3,272,854 | 9/1966 | Covey et al. | 424/303 |
| 3,363,003 | 1/1968 | Bolhofer | 260/609 F |
| 3,506,682 | 4/1970 | Fried | 260/613 |
| 3,715,401 | 2/1973 | Schroeter | 260/613 R |
| 3,957,885 | 5/1976 | Karrer et al. | 260/613 R |
| 3,962,459 | 6/1976 | Kathawala | 260/613 R |
| 3,963,786 | 6/1976 | Karrer et al. | 260/609 F |
| 4,017,549 | 4/1977 | Karrer et al. | 260/613 R |
| 4,051,173 | 9/1977 | Schacht et al. | 260/613 R |
| 4,057,587 | 11/1977 | Karrer et al. | 260/613 R |
| 4,080,474 | 3/1978 | Hindley et al. | 260/613 R |
| 4,085,149 | 4/1978 | Kathawala | 260/613 R |

*Primary Examiner*—Donald G. Daus
*Assistant Examiner*—M. C. Eakin
*Attorney, Agent, or Firm*—Theodore O. Groeger

[57] ABSTRACT

The invention relates to novel etherified cycloalkanols of the formula

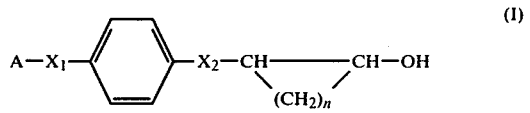

wherein $X_1$ represents oxygen, sulphur or methylene, $X_2$ represents oxygen or sulphur, A represents an unsubstituted or substituted phenyl radical and n is an integer from 1 to 10 inclusive, and processes for the production thereof.

These compounds, especially 2-(4-phenoxyphenoxy)-cyclo-pentan-1-ol, effect a lowering of the lipid content in the blood serum. They are also intermediates for the production of insecticidal cyclopropanecarboxylic acid esters.

9 Claims, No Drawings

ETHERIFIED CYCLOALKANOLS

The invention relates to new etherified cycloalkanols, in particular those of the formula (I)

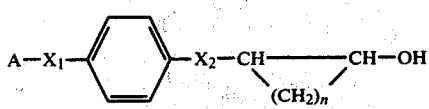

wherein $X_1$ represents oxygen, sulphur or methylene, $X_2$ represents oxygen or sulphur, A represents an unsubstituted or substituted phenyl radical, and n is an integer from 1 to 10 inclusive, and to a process for their production as well as to pharmaceutical preparations which contain these compounds and to the use thereof, preferably in the form of pharmaceutical preparations.

Throughout this specification, radicals and compounds qualified by the term "lower" preferably contain not more than 7, especially not more than 4, carbon atoms.

A substituted phenyl radical A is a mono-, di- or poly-substituted phenyl radical. As substituents there may be mentioned in particular: halogen with an atomic number up to 35 inclusive, lower alkyl, lower alkoxy or trifluoromethyl.

Lower alkyl is for example n-propyl, isopropyl, n-butyl, isobutyl, sec-butyl, tert-butyl, n-pentyl, isopentyl, n-hexyl, isohexyl or n-heptyl, but especially methyl or ethyl.

Lower alkoxy is for example n-propoxy, isopropoxy or n-butyloxy, but especially methoxy or ethoxy.

Halogen represents fluorine or bromine, but preferably chlorine.

Preferably $X_2$ and the hydroxyl group are in the transposition to each other.

The compounds of the present invention possess valuable pharmacological properties. Thus they effect a lowering of the lipid content in the blood serum, as can be demonstrated for example in male rats which over the course of 3 days receive a daily dose of 10 to 200 mg/kg of the test substances and on the fourth day two such doses, and subsequent determination of the cholesterol and triglyceride concentration in the blood serum. Accordingly, the novel compounds can be used as agents for alleviating hyperlipidemia and for the treatment of disturbed lipid metabolism.

However, the compounds of the invention can also be used as intermediates, in particular for the production of cyclopropanecarboxylic acid esters which are suitable for controlling a variety of animal and plant pests, especially for controlling representatives of the order Acarina of the families:

Ixodidae, Argasidae, Tetranychidae, Dermanyssidae, as well as insects of the families: Acrididae, Blattidae, Gryllidae, Gryllotalpidae, Tettigoniidae, Cimicidae, Pyrrhocoridae, Reduviidae, Aphididae, Delphacidae, Diaphididae, Pseudococcidae, Chrysomilidae, Coccinellidae, Bruchidae, Scarabaidae, Dermestidae, Tenebrionidae, Curculionidae, Tincidae, Noctuidae, Lymantriidae, Pyralidae, Galleridae, Culicidae, Tipulidae, Stomoxydae, Muscidae, Calliphoridae, Tryperidae or Pulicidae.

The invention relates in particular to compounds of the formula (II)

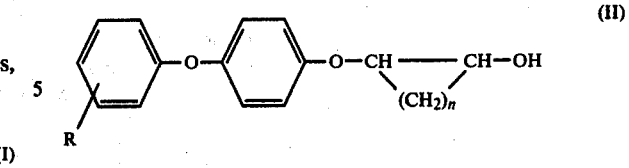

wherein R represents hydrogen or chlorine and n is 3, 4 or 5.

Primarily, the invention relates to 1-(4-phenoxyphenoxy)cyclopentan-2-ol.

The invention also relates preferably to the compounds of the formula

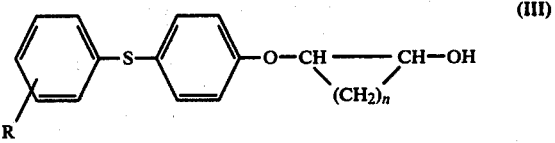

wherein R represents hydrogen or chlorine and n is 3, 4 or 5, or also to the compounds of the formula

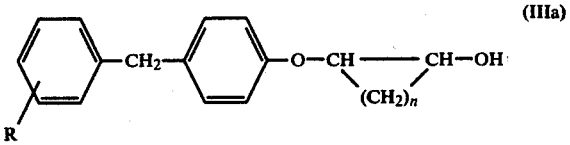

wherein R represents hydrogen or chlorine and n is 3, 4 or 5.

Most particularly, the invention relates to the novel compounds described in the Examples.

The novel compounds are obtained in a manner which is known per se, for example by reacting a compound of the formula (IV)

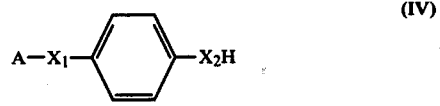

wherein A, $X_1$ and $X_2$ are as defined in formula (I), or a salt thereof, with a compound of the formula (V)

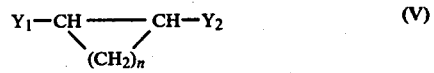

wherein $Y_1$ represents a free or reactive esterified hydroxyl group, and $Y_2$ represents a hydroxyl group which may or may not be protected, or $Y_1$ and $Y_2$ together represent an epoxy group or a carbonyldioxy group of the formula $-OC(O)O-$, and, in resulting compounds, removing a protective group which may be present, and, if desired, separating a mixture of isomers obtained by the process of the invention into the individual isomers.

Salts of compounds of the formula (IV) are in particular metal salts, especially alkali metal salts, for example sodium or potassium salts, which are usually prepared in situ.

A reactive esterified hydroxyl group is a particular one which is esterified with a strong acid, as with a strong inorganic or organic acid. Examples of strong inorganic acids are in particular hydrohalic acids, such as hydrochloric or hydrobromic acid; or sulphuric acid, and examples of organic acids are in particular sulphonic acids, such as a benzenesulphonic acid which may be substituted by halogen, lower alkyl or lower alkoxy, for example p-toluenesulphonic acid or p-methoxybenzenesulphonic acid; or an alkanesulphonic acid, for example methane- or ethanesulphonic acid.

A protected hydroxyl group is in particular an esterified hydroxyl group, for example an acyloxy group, such as a lower alkanoyloxy group, for example an acetoxy or benzoyloxy group, or an etherified hydroxyl group, for example a tetrahydropyranyloxy group or an aralkoxy group, such as the benzyloxy group.

The reaction can be carried out in a manner which is known per se. It is preferably carried out in the presence of a base, especially an inorganic base, such as a hydroxide, carbonate or hydride of an alkali metal or alkaline earth metal, for example sodium or potassium hydroxide, sodium or potassium hydride or sodium or potassium carbonate, or an organic base, such as piperidine, quinoline, or a tri-lower alkylamine, for example trimethylamine, triethylamine or dimethyl isopropylamine. However, the reaction can also be carried out in the presence of a carbodiimide, such as dicyclohexylcarbodiimide, in the presence of copper chloride, and in an inert solvent such as acetone or dimethylsulfoxide. The reaction can also be carried out in a higher boiling solvent, such as xylene, toluene or quinoline, at elevated temperature, for example between 80° and 200° C., or in the absence of a solvent.

A protected hydroxyl group can be set free in a manner which is known per se, for example by hydrolysis or hydrogenolysis.

The starting materials to be used for this reaction are known or they can be obtained in a manner which is known per se.

The novel compounds can however also be obtained by reducing the keto group in a compound of the formula (VI)

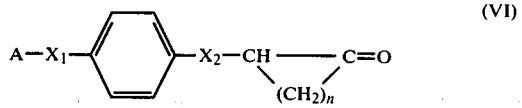

to the carbinol group in a manner which is known per se, and, if desired, separating a resulting isomer mixture into the individual isomers.

The reduction can be carried out in conventional manner, for example with catalytically activated hydrogen, for example in the presence of Raney nickel or of a palladium catalyst, such as palladium or charcoal, or with metal hydrides, such as sodium borohydride, lithium aluminium hydride or diborane, in the presence of an inert solvent, such as water, an alcohol, for example methanol or ethanol, or an ether, such as diethyl ether or tetrahydrofurane.

The starting material employed in this method is obtained in a manner which is known per se, for example by reaction of a keto-cycloalkanol, or a reactive ester thereof, with a compound of the formula IV in the manner described above, or by reaction of a compound of the formula IV with a reactive ester of a 3-hydroxycycloalkene and subsequent oxidation of the double bond, for example with mercury(II) nitrate or acetate in water, or with a peracid, such as peracetic acid. The resulting starting material of the formula (VI) can, if desired, be reduced without isolation.

The novel compounds can be obtained as isomer mixtures, such as racemates or diastereoisomer mixtures, or in the form of the pure isomers, such as the optically active components. The separation of isomer mixtures can be effected by known methods. Diastereoisomer mixtures can be separated into the individual isomers for example on the basis of physico-chemical differences, such as different solubilities, for example by fractional crystallisation or distillation, or by chromatography.

Racemates can be resolved into the optically active antipodes, for example by esterification of the alcohol-racemate with an optically active acid, for example optically active camphorsulphonic acid, separation of the resulting ester-diastereoisomer mixture and saponification of the ester, or by esterification of the alcohol-racemate with a dicarboxylic acid, wherein only one carboxyl group is esterified, formation of a salt of the resulting monoester acid racemate with a suitable optically active base, for example optically active brucine, α-phenylethylamine or ephedrine, separation of the resulting salt-diastereoisomer mixture and saponification of the resulting ester salt. Advantageously, that isomer which possesses the pharmacologically more valuable properties is isolated.

The processes described above are carried out by methods which are known per se, in the absence or preferably in the presence of diluents or solvents, if necessary with cooling or heating, under elevated pressure and/or in an inert gas atmosphere, such as a nitrogen atmosphere.

The invention also relates to those embodiments of the invention in which a compound obtainable as intermediate in any stage of the process is used as starting material and the remaining process steps are carried out, or in which the process is interrupted at any stage, or in which a starting material is formed under the reaction conditions or is used in the form of a reactive derivative or salt. Preferably, those starting materials are chosen which result in the compounds referred to above as especially valuable being obtained.

The present invention also relates to hypolipidemic pharmaceutical preparations which contain compounds of the formula I. The pharmaceutical preparations of the invention are administered enterally, such as orally or rectally, as well as parenterally, to warm-blooded animals, and contain the pharmacologically active substance by itself or together with a pharmaceutically acceptable carrier. The dosage of the active substance depends on the species of the warm-blooded animal, age, and individual condition, as well as on the mode of application.

The pharmaceutical preparations of the present invention can be for example in dosage unit forms, such as sugar-coated tablets, tablets, capsules, suppositories or ampoules, and are manufactured in a manner which is known per se, for example by conventional mixing, granulating, sugar-coating, dissolving or lyophilising methods. Pharmaceutical preparations in particular for oral administration can be obtained by combining the active substance with solid adjuncts, if appropriate granulating a resulting mixture, and processing the mixture or granulate, if necessary or desired after addition of suitable adjuvants, to tablets or sugar-coated cores.

Suitable adjuncts for solid preparations for oral administration are in particular fillers, such as sugar, for example, lactose, saccharose, mannitol or sorbitol, cellulose preparations and/or calcium phosphates, e.g. tricalcium phosphate or calcium hydrogen phosphate, also binders such as starch pastes, for example maize, corn, rice or potato starch paste, gelatin, tragacanth, methyl cellulose, hydroxypropylmethylcellulose, sodium carboxymethylcellulose and/or polyvinylpyrrolidone, and/or, if desired, disintegrators, such as the above starches, also carboxymethyl starch, crosslinked polyvinylpyrrolidone, agar, alginic acid or a salt thereof, such as sodium alginate. Adjuncts are chiefly glidants and lubricants, for example, silicic acid, talc, stearic acid or salts thereof, such as magnesium stearate or calcium stearate, and/or polyethylene glycol. Sugar-coated tablet cores are provided with suitable coatings that can be resistant to gastric juices, using, inter alia, concentrated sugar solutions which may contain gum arabic, talc, polyvinylpyrrolidone, polyethylene glycol and/or titanium dioxide, shellac solutions in suitable organic solvents or solvent mixtures or, for the preparation of coatings resistant to gastric juices, solutions of suitable cellulose preparations, such as acetylcellulose phthalate or hydroxypropylmethylcellulose phthalate. Dyes or pigments can be added to the tablets or sugar-coated tablet cores, for example to identify or indicate different doses of active ingredient.

The pharmaceutical preparations contain from about 0.1% to 100%, in particular from about 1% to about 50%, of the active substance. The single dose for a warm-blooded animal having a body weight of about 70 kg is between 0.1 and 0.75 g, and the daily dose is between 0.2 and 1 g. The invention also relates to novel cyclopropanecarboxylic acid esters of the formula VII

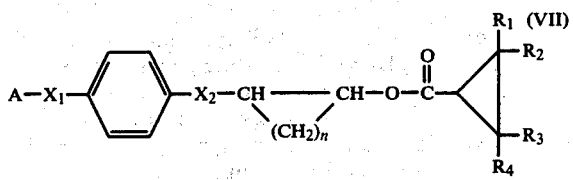

wherein A, $X_1$, $X_2$ and n are as defined in formula (I) and each of $R_1$, $R_2$, $R_3$ and $R_4$ represents hydrogen, methyl, or chlorine, to the production of these compounds and to their use in pest control.

Preferred compounds on account of their action are those of the formula VII, wherein A represents phenyl, and $X_1$ and $X_2$ represent oxygen. Compounds of the formula VII, wherein $R_1$, $R_2$, $R_3$ and $R_4$ represent either hydrogen or methyl, are also preferred. Compounds of the formula VII, wherein $R_1$ and $R_2$ represent chlorine and $R_3$ and $R_4$ represent methyl, are also to be highlighted.

As already stated above, these esters are eminently suitable for controlling a variety of animal and plant pests.

The compounds of the formula VII are prepared by methods which are known per se, for example as follows:

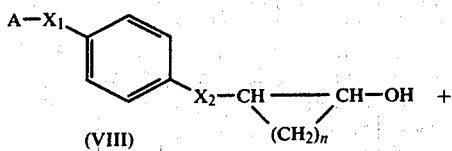

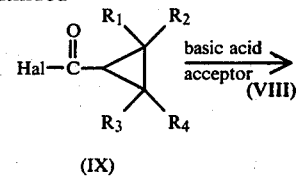

In the above formula (IX), Hal represents halogen, especially chlorine or bromine.

Examples of suitable basic acid acceptors are: tertiary amines, such as trialkylamines, for example ethyl diisopropylamine; pyridine; dialkyl anilines; also inorganic bases, such as hydrides, hydroxides, alkoxides and carbonates of alkali metals and alkaline earth metals.

The process is normally carried out at a temperature of about 10° to 100° C., with acid halides usually at 0° to 30° C., and with acid anhydrides usually at 70° to 100° C., under normal pressure and in an inert solvent or diluent. Suitable solvents or diluents are for example: benzene, toluene, xylene, paraffin hydrocarbons, such as hexane or heptane; ethers, such as diethyl ethers, tetrahydrofurane, dioxane, dimethoxy ethane; and esters, such as ethyl acetate.

The insecticidal action can be substantially broadened and adapted to prevailing circumstances by the addition of other insecticides and/or acaricides. Examples of suitable additives are: organic phosphorus compounds, nitrophenols and derivatives thereof, formamidines, ureas, pyrethroids, carbamates, and chlorinated hydrocarbons.

The compounds of the formula VII may be used as pure active substance or together with suitable carriers and/or adjuvants. Suitable carriers and adjuvants can be solid or liquid and correspond to the substances conventionally used in the art of formulation, for example natural or regenerated substances, solvents, dispersants, wetting agents, tackifiers, thickeners, binders and/or fertilisers.

For application, the compounds of the formula VII may be processed to dusts, emulsifiable concentrates, granules, dispersions, sprays, to solutions, or suspensions, in the conventional formulation which is commonly employed in application technology.

The compositions of the present invention are manufactured in known manner by homogeneously mixing and/or grinding the compounds of the formula VII with the suitable carriers, with or without the addition of dispersants or solvents which are inert to the compounds.

The compounds of the formula VII may be processed to the following formulations:
Solid formulations:
  dusts, tracking powders and granules (coated granules, impregnated granules and homogeneous granules).
Liquid formulations:
  (a) formulations which are dispersable in water: wettable powders, pastes and emulsions;
  (b) solutions.

The content of active substances in the above described compositions is between 0.1% and 95%.

The following Examples illustrate the invention.

EXAMPLE 1

A mixture of 52 g of 4-hydroxydiphenyl ether and 23.5 g of 1,2-epoxycyclopentane is heated to 150° C. To this melt are added in the course of 25 minutes 6.7 g of 90% potassium hydroxide powder and the mixture is stirred for one hour at 130° C. After cooling, the reaction mixture is taken up in ether/hexane (1:1) and the organic solution is washed 4 times with 10% potassium hydroxide solution and 3 times with saturated sodium chloride solution. The organic phase is dried over sodium sulphate and concentrated by rotary evaporation under reduced pressure. Distillation of the crude product yields 2-(4-phenoxyphenoxy)-cyclopentan-1-ol as a colourless oil with a boiling point of 181°–185° C./0.001 torr and a refractive index of $n_D^{20} = 1.5812$.

2-(4-Phenoxyphenoxy)-cyclohexan-1-ol, which melts at 62°–65° C. after recrystallisation from hexane, and 2-(4-benzylphenoxy)-cyclohexan-1-ol, which melts at 78°–80° C. after recrystallisation from isopropanol, are obtained in analogous manner.

EXAMPLE 2

Starting from the corresponding starting materials, the following compounds are obtained by a procedure analogous to that described in Example 1:

2-(4-phenylmercaptophenoxy)-cyclopentan-1-ol, as a colourless oil with a refractive index $n_D^{20} = 1.6217$, 2-(4-benzylphenoxy)-cyclopentane-1-ol, as an oil with a refractive index $n_D^{20} = 1.5794$, 2-[4-chlorophenoxy)-phenoxy]cyclopentan-1-ol, m.p. 53°–55° C., 2-[4-(4-chlorophenoxy)phenoxy]-cyclohexan-1-ol, m.p. 82°–83° C., 2-(4-phenylmercaptophenoxy)-cyclohexan-1-ol, m.p. 79°–81° C., 2-[4-(2,4-dichlorophenoxy)-phenoxy]-cyclohexan-1-ol, m.p. 84°–86° C., 2-[4-(2,4-dichlorophenoxy)-phenoxy]-cyclopentan-1-ol, as an oil with a refractive index $n_D^{20} = 1.5946$, 2-[4-(2-methylphenoxy)-phenoxy]-cyclohexan-1-ol, m.p. 73°–75° C., 2-[4-(4-chlorophenylmercapto)-phenoxy]-cyclohexan-1-ol, m.p. 90°–92° C., 2-(4-phenoxyphenylmercapto)-cyclohexan-1-ol, as an oil with a refractive index $n_D^{20} = 1.6051$, 2-(4-phenoxyphenylmercapto)-cyclopentan-1-ol, as an oil with a refractive index $n_D^{20} = 1.6101$, 2-[4-(2-methylphenoxy)-phenoxy]-cyclopentan-1-ol, as an oil with a refractive index $n_D^{20} = 1.5757$, or 2-[4-(4-chlorophenylmercapto)-phenoxy]-cyclopentan-1-ol, as an oil with a refractive index $n_D^{20} = 1.6212$.

EXAMPLE 3

A solution of 3.78 g of sodium borohydride in 10 ml of water is added at room temperature to a solution of 8.04 g of 2-(4-phenoxyphenoxy)-cyclopentan-1-one in 60 ml of methanol. The reaction mixture is stirred for 15 hours at room temperature and then concentrated under reduced pressure. The residue is poured into ice-water and extracted with ether. The organic phase is washed twice with saturated sodium chloride solution, dried over sodium sulphate and concentrated by rotary evaporation. Fractional distillation of the residue yields 2-(4-phenoxyphenoxy)-cyclopentan-1-ol as a colourless oil with a boiling point of 181°–185° C./0.001 torr.

The starting material can be obtained for example as follows: To a solution of 18.6 g of 4-phenoxyphenol in 80 ml of acetone are added 15.2 g of anhydrous potassium carbonate and the reaction mixture is refluxed for 1 hour. Then 17.3 g of 2-bromo-cyclopentanone are added dropwise and the reaction mixture is refluxed for 20 hours, then cooled and filtered. The filtrate is concentrated by rotary evaporation and the residual oil is taken up in ether. The solution is washed 4 times with 10% potassium hydroxide solution and twice with saturated sodium chloride solution, dried over sodium sulphate and concentrated by rotary evaporation. The resulting crude 2-(4-phenoxyphenoxy)-cyclopentan-1-one is used for the above described reaction without purification.

EXAMPLE 4

2-(4-Phenoxyphenoxy)-cyclohexan-1-one, with a melting point of 103°–105° C. and which is reduced, as described above, to give the corresponding 2-(4-phenoxyphenoxy)-cyclohexan-1-ol with a melting point of 62°–65° C., is obtained by a procedure analogous to that described in Example 3 and starting from the corresponding starting materials.

EXAMPLE 5

While cooling with ice, 6.7 g of 90% potassium hydroxide powder are added to a solution of 18.6 g of 4-phenoxyphenol in 120 ml of dimethyl sulphoxide and the mixture is stirred for ½ hour at room temperature. Then 16.3 g of 2-acetoxy-cyclopentyl chloride are added in the course of 20 minutes and the reaction mixture is stirred for about 18 hours at 50° C., then poured into ice-water. After extraction with ether, the organic phase is washed with water and once with saturated sodium chloride solution, dried over sodium sulphate and concentrated. After fractional distillation, the resulting 1-acetoxy-2-(4-phenoxyphenoxy)-cyclopentane is in the form of a colourless oil with a refractive index of $n_D^{20} = 1.5560$.

A solution of 1.68 g of potassium hydroxide in 20 ml of water is added at room temperature to a solution of 6.24 g of 1-acetoxy-2-(4-phenoxyphenoxy)-cyclopentane in 50 ml of ethanol. The mixture is then refluxed for 3 hours and, after cooling, concentrated to 166 of its original volume by rotary evaporation. The residue is poured into ice-water. After extraction with ether, the organic phase is washed three times with saturated sodium chloride solution, dried over sodium sulphate and concentrated by rotary evaporation. Distillation of the residue yields 2-(4-phenoxyphenoxy)-cyclopentan-1-ol as a colourless oil with a boiling point of 181°–185° C./0.001 torr.

EXAMPLE 6

A solution of 12.6 g of 3-(4-phenoxyphenoxy)-cyclopenten-1-ene in 25 ml of tetrahydrofurane is added dropwise in the course of 1 hour to a mixture of 15.9 g of mercury(II) acetate, 35 ml of water and 50 ml of tetrahydrofurane. The mixture is stirred for about 15 hours at room temperature, then 50 ml of 3 N sodium hydroxide solution are added dropwise in the course of 1½ hours, followed by the dropwise addition in the course of 1 hour of 50 ml of a 0.5 N solution of sodium borohydride in 3 N sodium hydroxide solution. The reaction mixture is stirred for 2 hours at room temperature and precipitated mercury is removed by filtration. The filtrate is poured into ice-water and, after extraction with ether, the organic phase is washed with saturated sodium chloride solution, dried over sodium sulphate and concentrated by rotary evaporation. Fractional distillation of the residue yields 2-(4-phenoxyphenoxy)cyclopentan-1-ol as a colourless oil with a boiling point of 181°–185° C./0.001 torr.

The starting material used in this Example can be prepared for example as follows:

To a solution of 18.6 g of 4-phenoxyphenol in 80 ml of acetone are added 15.2 g of anhydrous potassium carbonate and the reaction mixture is refluxed for 1 hour. Then 15.7 g of cyclopent-2-enyl bromide are added dropwise and the reaction mixture is refluxed for a further 16 hours, cooled, and filtered. The filtrate is concentrated by rotary evaporation and the residual oil is taken up in ether. The organic phase is washed 4 times with 10% potassium hydroxide solution and twice with saturated sodium chloride solution, dried over sodium sulphate and concentrated by rotary evaporation. The resulting 3-(4-phenoxyphenoxy)-cyclopentene can be used without further purification.

EXAMPLE 7

A mixture of 18.6 g of 4-phenoxyphenol, 12.8 g of 1,2-carbonyldioxycyclopentane and 4.6 g of triethylammonium iodide is stirred for 7 hours at 150° C. After cooling, the reaction mixture is taken up in chloroform. The solution is washed with water and once with saturated sodium chloride solution, dried over sodium sulphate and concentrated by rotary evaporation. Fractional distillation of the residue yields (2-(4-phenoxy-phenoxy)-cyclopentan-1-ol as a colourless oil with a melting point of 181°–185° C./0.001 torr.

EXAMPLE 8

Preparation of the compound of the formula

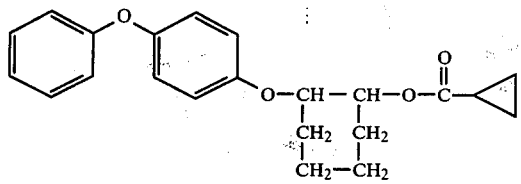

To a solution of 28.3 g of 2-(4-phenoxy)-phenoxy-cyclohexanol in 150 ml of anhydrous benzene are added 12.1 g of triethylamine and then, with stirring, 11.5 g of cyclopropanecarboxylic chloride are added dropwise at 15°–20° C. in the course of 1 hour. The reaction mixture is further stirred for 24 hours at room temperature, then washed neutral in succession and repeatedly with water, dilute hydrochloric acid, 10% sodium carbonate solution and finally with saturated sodium chloride solution. The organic phase is separated, dried over sodium sulphate and freed from solvent in vacuo. The oily residue is further purified by chromatography on silica gel (eluant:methyl acetate/hexane 1:4), yielding the compound of the formula IV with a refractive index of $n_D^{20}$:1.5542.

The following compounds are also prepared in analogous manner:

| | physical data |
|---|---|
| (structure) | $n_D^{20}$ : 1,5590 |
| (structure) | $n_D^{20}$ : 1,5574 |
| (structure) | $n_D^{20}$ : 1,5562 |
| (structure) | $n_D^{20}$ : 1,5421 |

-continued

| | physical data |
|---|---|
| 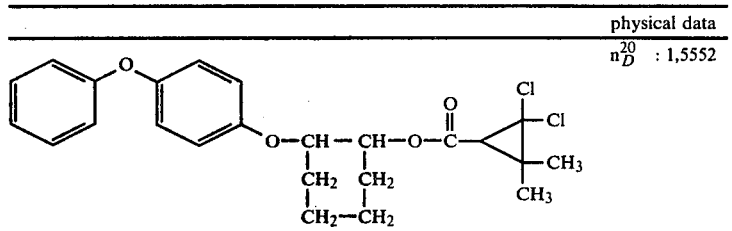 | $n_D^{20} : 1.5552$ |

We claim:

1. A hypolipidemic pharmaceutical preparation containing an effective, the lipid content of the blood serum lowering amount of a compound of the formula I $$A-X_1-\underset{(CH_2)_n}{\underset{\diagdown \quad \diagup}{\text{C}_6H_4}}-X_2-CH\text{------}CH-OH \quad (I)$$

wherein A is phenyl unsubstituted or substituted by at least one member selected from the group consisting of halogen with an atomic number up to 35 inclusive, lower alkyl, lower alkoxy and trifluoromethyl, $X_1$ is oxygen, sulphur or methylene, $X_2$ is oxygen or sulphur and n is an integer from 1 to 10 inclusive, together with a pharmaceutical carrier.

2. A preparation as claimed in claim 1, containing a compound of the formula I wherein A is phenyl or chlorophenyl, $X_1$ and $X_2$ each represent oxygen and n is 3, 4 or 5.

3. A preparation as claimed in claim 1, containing a compound of the formula I wherein A is phenyl or 4-chlorophenyl, $X_1$ and $X_2$ each represent oxygen and n is 3.

4. A preparation as claimed in claim 1, containing a compound of the formula I wherein A is phenyl or 4-chlorophenyl, $X_1$ and $X_2$ each represent oxygen and n is 4.

5. A preparation as claimed in claim 1, containing a compound of the formula I wherein A is phenyl or chlorophenyl, $X_1$ represents sulphur, $X_2$ represents oxygen and n is 3, 4 or 5.

6. A preparation as claimed in claim 1, containing a compound of the formula I wherein A is phenyl or 4-chlorophenyl, $X_1$ represents sulphur, $X_2$ represents oxygen and n is 3 or 4.

7. A preparation as claimed in claim 1, containing a compound of the formula I wherein A is phenyl or chlorophenyl, $X_1$ represents methylene, $X_2$ represents oxygen and n is 3, 4 or 5.

8. A preparation as claimed in claim 1 containing a compound of the formula I, wherein A is phenyl, $X_1$ is methylene, $X_2$ is oxygen and n is 3 or 4.

9. A method of treating hyperlipidemia in warm-blooded animals, which comprises administering to said animals enterally or parenterally an effective amount of a preparation as claimed in claim 1.

* * * * *